US006257889B1

(12) United States Patent
Boston (10) Patent No.: US 6,257,889 B1
(45) Date of Patent: Jul. 10, 2001

(54) DENTAL BUR AND METHOD

(75) Inventor: Daniel W. Boston, St. Davids, PA (US)

(73) Assignee: Temple University - of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/277,216

(22) Filed: Mar. 25, 1999

(51) Int. Cl.[7] ............................................. A61C 3/00
(52) U.S. Cl. ................................. 433/165; 433/166
(58) Field of Search ................................. 433/165, 166, 433/142, 147, 102

(56) References Cited

U.S. PATENT DOCUMENTS

| | | | |
|---|---|---|---|
| 749,624 | * | 1/1904 | McCullough ........................ 433/165 |
| 1,813,741 | * | 7/1931 | Harper ................................. 433/165 |
| 2,715,772 | * | 8/1955 | Fritz .................................... 433/165 |
| 4,284,406 | * | 8/1981 | Hughes ................................ 433/165 |
| 5,299,937 | * | 4/1994 | Gow .................................... 433/165 |

FOREIGN PATENT DOCUMENTS

2744564 * 4/1979 (DE) ..................................... 433/165

OTHER PUBLICATIONS

Teledyne Densco, product literature, Denver Colo, ©1983 Teledyne, Inc.*

* cited by examiner

*Primary Examiner*—Ralph A. Lewis
(74) *Attorney, Agent, or Firm*—Wildman, Harold, Allen & Dixon (57) ABSTRACT

A dental bur for use in examining anomalies and in restoration of decayed areas of teeth with a bur head having a generally elongate conical shaped body with a base and an opposed vertex. Cutting members are located about the outer surface of the body between the base and vertex and extend along the outer surface of the bur head which has a length of at least 1.5 millimeters.

46 Claims, 5 Drawing Sheets

DENTAL BUR AND METHOD

BACKGROUND OF THE INVENTION

The present invention relates generally to devices used in the diagnosis of anomalies in teeth and, more specifically, to dental burs used in penetrating the surface of teeth to facilitate the diagnosis by a practitioner.

Incipient initial carious lesions in dentin beneath enamel pits and fissures of teeth often can be very difficult to diagnose, even with good visual access and with the use of an explorer tool having a sharp pointed tip. The difficulty in diagnosis is present even with excellent radiographs. In teeth with deep pits and fissures, dentinal caries can develop at the dentinoenamal junction and progress further into dentin with minimal or no clinically-evident signs of disease in the overlying enamel. This phenomena in the art is referred by the term "hidden caries".

One non-treatment modality of dealing with this problem is the "watch and wait" process and in the event that cavitation occurred, a diagnosis is made via a visual inspection and explorers and radiographs. At this stage the lesion is more advanced and requires a less conservative treatment to treat the lesion.

A preemptive aggressive treatment resulting in a classical amalgam restoration for what is believed to be an incipient carious lesion in the dentin between enamel pits and fissures results in a significant removal of tooth because amalgam restorations require a minimum of approximately one and one-half millimeters in depth to establish the proper holding characteristics for the amalgam restoration.

With the advent of the widespread exposure of patients to topical fluorides, the difficulty in identifying incipient carious lesions has been exacerbated. This occurs because the fluoride makes the enamel immediately adjacent to pits and fissures relatively resistant to carious lesions, while not affecting the dentin. Thus, the dentin caries can develop at the dentinoenamal junction and progress further into dentin with minimal or no clinically evident signs in the overlying enamel.

Minimally invasive techniques for diagnosing initial carious lesions have included the use of small ball-shaped round diamond or carbide burs having a diameter of approximately 0.25 millimeters to 1 millimeter. The problem with using such round diamond burs is that they do not leave the examined area with a smooth surface rendering further examination by the practitioner using an explorer device difficult to assess the existence of carious lesions. Another problem with the small round diamond bur is that it does not lend itself to plunge cutting for the examination of carious lesions deep in dentin beneath the tooth enamel. The short length of such conventional round diamond burs often does not provide sufficient depth for cutting of the tooth enamel. Furthermore, round burs do not cut smooth, flat, axial walls and leave unsupported enamel rods. Moreover, when inserting a typical round diamond bur into a tooth, the wide cutting portion at the diameter of the round bur often disadvantageously removes more of the patient's tooth than is required for certain dental procedures.

Another approach to investigating insidious carious lesions is the use of an air abrasion tool. Disadvantageously, treatment with the air abrasion tool is costly because it requires a large investment of capital for the air abrasion equipment. Furthermore, the air abrasion tool is not easy to control and creates a significant amount of debris in the dental work area, particularly when examining relatively large caries in a tooth. Moreover, air abrasion requires a significant learning process to learn a proper preparation technique.

The present invention is directed to overcoming, or at least reducing the problems set forth above.

SUMMARY OF THE INVENTION

The problems noted above are solved in accordance with the invention and a technical advance is achieved in the art, by providing a dental bur and method for effectively performing dental procedures to teeth. The elongate dental bur is formed to be used in both diagnostic procedures for examining anomalies in a tooth and restoration procedures to overcome and repair tooth decay.

In particular, the dental bur has a bur head with a body having a base, an opposed vertex and a plurality of cutting members located at an outer surface of the body without least a portion of the cutting members being disposed between the base and vertex and extending along the outer surface with the bur head being at least 1.5 millimeters in length. Preferably, the body and the cutting members are formed of a carbide material with the body of the bur head being generally conical in shape such that a maximum diameter of the bur head is proximate the base and the diameter of the bur head gradually decreases as the bur head extends toward the vertex. The dental bur is enabled to be securable to a handpiece which rotates the bur at a preselected rotational speed when in operation upon receipt of power from a dental unit connected with the handpiece.

BRIEF DESCRIPTION OF THE DRAWINGS

The foregoing objects and advantageous features of the invention will be explained in greater detail and others will be made apparent from the detailed description of the preferred embodiment of the present invention which is given with reference to the several figures of the drawing, in which.

DETAILED DESCRIPTION

Figure 1:
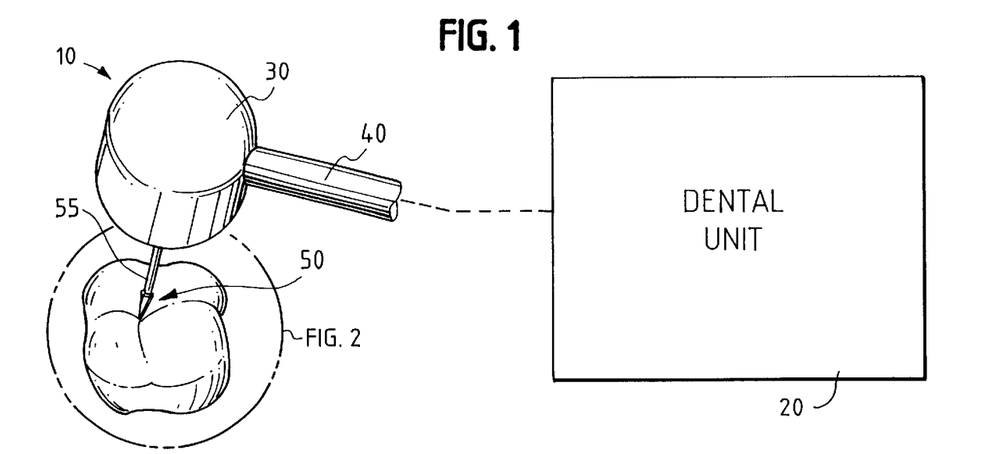
FIG. 1 is an illustrative diagram of a dental system with a dental bur secured to a high speed dental handpiece.
Figure 2:
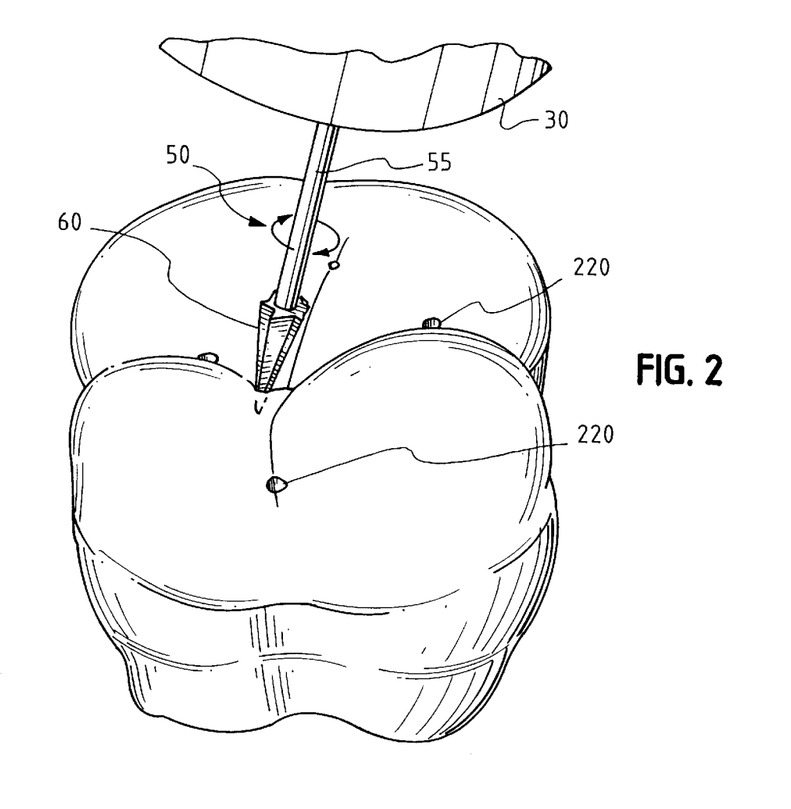
FIG. 2 is an enlarged perspective view of the circled area in FIG. 1 of the dental bur engaging a tooth.

Referring to FIGS. 1 and 2, a dental system 10 is shown having a dental unit 20 connected to a handpiece 30 via a hose 40. The dental unit 10 provides power to the handpiece 30. A dental bur 50 engages and is captively held by the handpiece 30 which rotates the dental bur 50 at a preselected rotational speed upon receipt of compressed air operating power from the dental unit 20 Preferably, the dental bur 50 rotates at speeds ranging from 300,000 to 350,000 rotations per minute. As seen in FIG. 2, the dental bur 50 has drive shaft 55 engaged with the hand unit 30 which provides the operative power from the dental unit 20 to rotate the bur head 60 and enable it to perform dental procedures on a tooth.

Figures 3, 4:
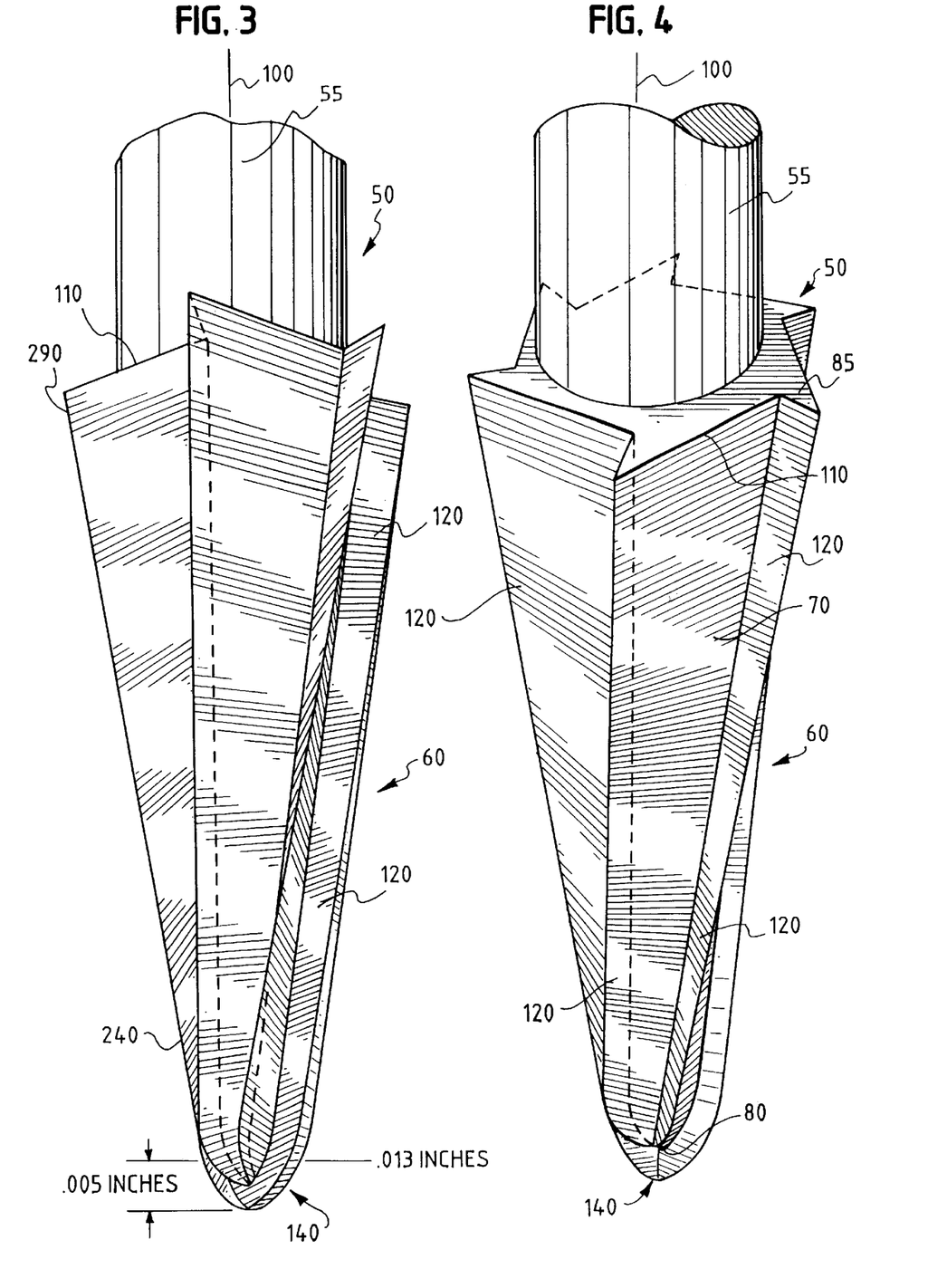
FIG. 3 is a front bottom perspective view of the dental bur of the present invention.
FIG. 4 is a top front perspective view of the dental bur of the present invention.

As shown in perspective views of FIGS. 3 and 4, the dental bur 50 includes a bur head 60 having a body 70 with a base 85 and an opposed vertex 80. A drive shaft 55 is coaxially aligned with a longitudinal axis 100 of the body 70 and extends outwardly from the base 85 for engaging the handpiece 30.

As shown in FIG. 3, the diameter of the head 60 of the dental bur 50 is 0.013 inches at a location measured 0.005 inches from the outer tip at the vertex 80 of the bur. The body 70 of the bur head 60 has a conical shape and a length measured along the longitudinal axis 100 of the body 70 preferably being 2.5 millimeters in length. The length of the bur head may selectively range from 1.5 to 3 millimeters. The base 85 has a diameter preferably being 1 millimeter in width to facilitate the use of an explorer to examine cuts in a tooth made by the dental bur 50. It is understood that variations to the diameter width at the base 85 of the bur head 60 may be made. However, in accordance with an aspect of the present invention the diameter width of the base is intended to be narrow such that the bur head has a slender conical shape and to conserve tooth enamel by avoiding the removal of excess tooth enamel which is more than needed to perform examination procedures. The bur head 60 is designed to be narrow and only wide enough to adequately enable an explorer tool (not shown) to be used in a cut for investigating potential decay. The diameter of the base 85 of the bur head may selectively range from 0.8 to 1.2 inches. The ratio of the maximum diameter of the body 70 measured perpendicular to the longitudinal axis 100 to the length of the body 70 measured along the longitudinal axis preferably is not greater than 2.8:1.

Figure 5:
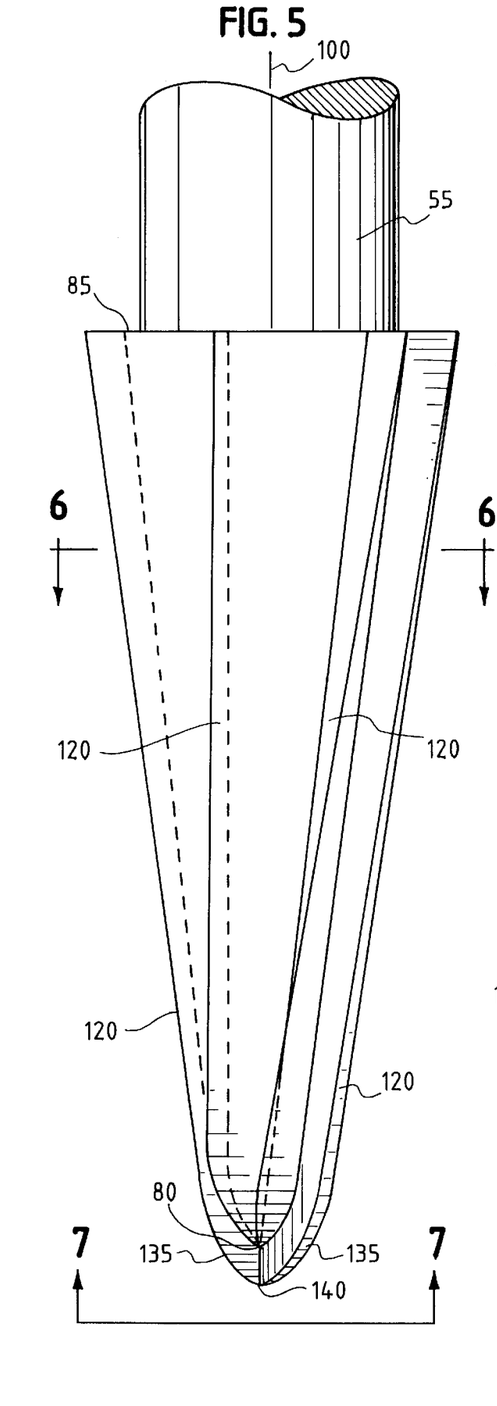
FIG. 5 is a front elevation view of the dental bur.

The bur head 60 body 70, FIGS. 3–5 includes an outer surface 110 having cutting members 120 extending outwardly from the outer surface of the body 70 of the and in which at least a portion of the cutting members are positioned between the base 85 and vertex 80 and extend along the outer surface for a distance of at least 1.5 millimeters measured along the longitudinal axis. Preferably, the body 70 and the elongate cutting members 120 of the head 60 are formed of a carbide material. The conical bur head 60 has its maximum diameter proximate the base 85 with the diameter of the bur head gradually decreasing as the body 70 extends toward the opposed vertex 80.

The cutting members 120 are preferably elongated carbide blades having a height extending outwardly from the body 70 of the bur head 60. As seen in FIGS. 4 and 5, the blades 120 are generally parallel to the longitudinal axis 100 of the body 70 at a helix angle of preferably two degrees. However, an acceptable range for the helix angle of the blades is zero degrees (0°) to twelve degrees (12°). Preferably six blades 120 are located the outer surface 110 of the body 70 with two opposing blades 135 of the six blades extending over the vertex 80 of the body 70 to form a drill tooth 140. The cutting members 120 provide a variable cutting intensity along the longitudinal axis 100 upon rotation of the dental bur 50 at a preselected speed. It is understood that diamonds or other durable cutting materials may selectively be exployed as cutting members at the outer surface of the bur head.

Figure 6:
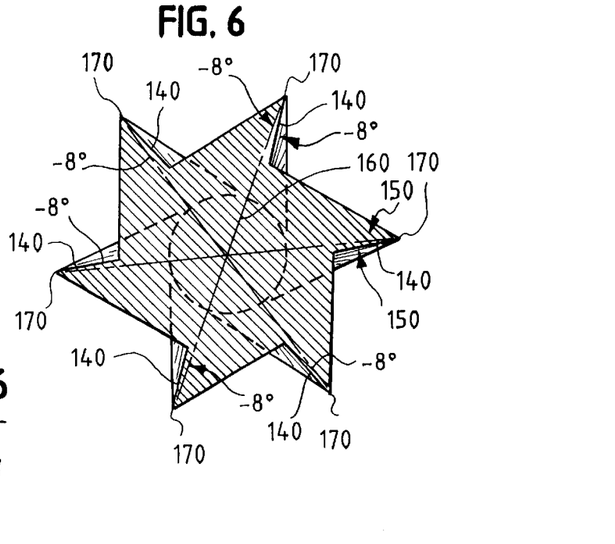
FIG. 6 is a cross sectional view of the dental bur head taken along line 6—6 of FIG. 5.

In FIG. 6, a cross sectional view along the line 6—6 of FIG. 5 is shown. Each of the six blades 120 has a rake face 140 that is the leading face of each blade. A rake angle 150 of each blade 120 is the angle of the rake face 140 of the blade to the cross-sectional axis or radius 160 of the dental bur 50 extending outwardly from the longitudinal axis of the dental bur. The apex 170 of each rake angle 150 is at a blade tip 180 in the cross section. The preferred rake angle 150 is minus eight degrees (–8°) for each of the blades of the bur head 60. The rake angle 150 for the blades of the bur head may selectively range from zero degrees (0°) to minus fifteen degrees (–15°).

Figure 7:
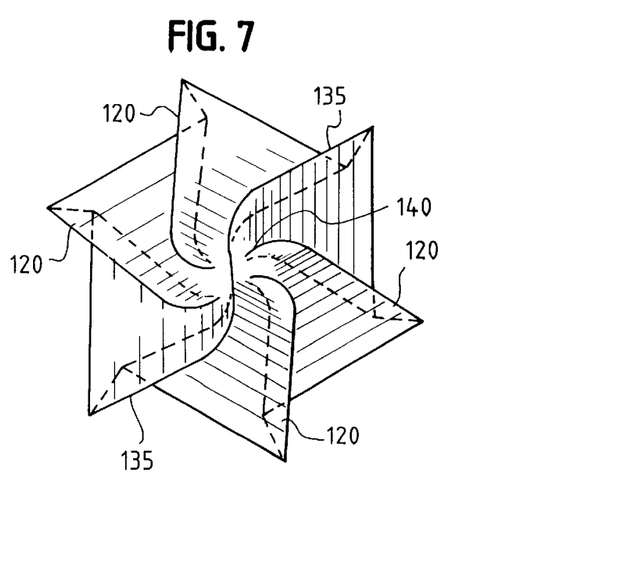
FIG. 7 is a bottom plan view of the dental bur head viewed from line 7—7 of FIG. 5.

As seen in FIGS. 5 and 7, an opposed pair of blades 135 extend over the vertex 80 of the body to form a drill tooth 140 at the vertex of the head. The remaining four blades 120 extend along the outer cutting surface of the head 60 to a location proximate the drill tooth at the vertex. The elongate blades 120 are connected at the body of the bur head 60 to establish a cutting surface such that the cutting intensity is variable along the longitudinal axis of the body (stronger a t the wide portion near the base) when the bur is rotated by the hand piece at a preselected rotational speed.

Figure 8:
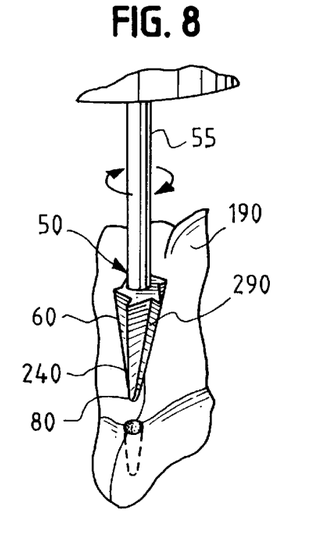
FIG. 8 is a plan elevational view of a tooth.

In accordance with the present invention, the dental bur 50 having an elongate conical bur head 60 is shaped to effectively perform various dental cutting procedures. The versatility of the dental bur 50 for use in treating anomalies in teeth can be seen with reference to FIGS. 8 through 16. In operation, the dental bur 50, FIG. 8, is utilized to perform diagnostic or examination procedures in identifying and determining the extent of decay of anomalies in a tooth 190. Upon examining any anomalies in the tooth 190, the same dental bur is utilized in performing restoration procedures (as described in FIGS. 13–16) to the tooth, thereby reducing or eliminating the need to repeatedly substitute and affix different dental burs to the high speed hand piece 30, FIG. 1, during the treatment process. The dental bur 50 is used to develop a cavity preparation of the overlying enamel.

Figure 9:
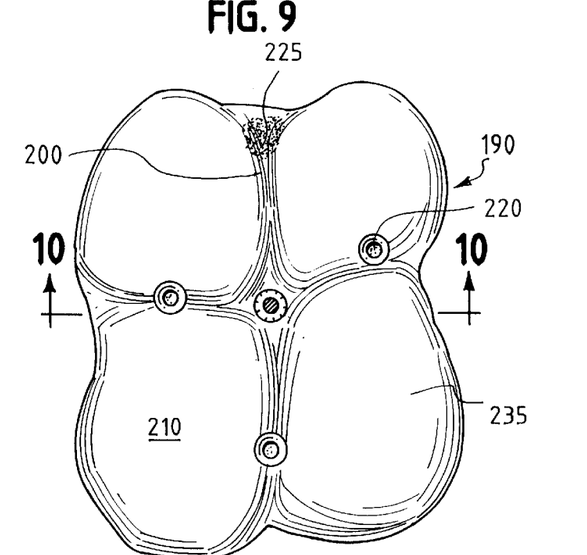
FIG. 9 is a perspective view illustrating the dental bur making an exploration cut to a tooth.

In performing diagnostic procedures, the tooth 190 is examined in order to identify and locate anomalies at the tooth. Once an anomaly is identified, the extent of decay is investigated by exploring the anomaly with the bur head 60 of the dental bur 50. As seen in FIG. 9, anomalies which are generally examined include a decalcified fissure 200 in the enamel surface 210 of the tooth 190, pits 220 (FIG. 2) in the enamel of the tooth, and discolorations 225 on the enamel of the tooth. A separate explorer tool (not shown) may also be used in examining anomalies, such as by inserting the explorer tool into pits in the enamel to see if the tool sticks, indicating decay.

Prior to exploring the anomaly with the dental bur 50, the approximate thickness of the enamel near the anomaly is determined. Various criteria including the location of the anomaly on the tooth, the type of tooth, radiographs of the tooth, the depth of the fissure on the tooth etc. may be used in determining the particular enamel thickness. As seen in FIG. 8, when examining the anomalies, a narrow portion 240 proximate the vertex 80 of the bur head 60 is applied to the anomaly. With the high speed handpiece 30, FIG. 1, operatively powered, the bur head 60 is directed to engage the anomaly to create a cut in the tooth in the area of the anomaly. Based on the thickness of a tooth enamel 250, FIGS. 10–12, in the region of the anomaly, the depth of the cut is determined. The cutting members 120, FIGS. 3–4, are positioned to cut and remove anomalies in the tooth to a preselected distance. Preferably, the bur head 60 is formed to extend to at least a junction 255 of the enamel portion 250 and a dentin portion 265 of the tooth as seen in FIG. 11. The depth of the cut in the enamel 250 is gauged by observing the length of the bur head 60 as seen in FIG. 10 which extends above the outer surface 235 of the tooth enamel 250 and factoring in the thickness of the enamel at the location of the anomaly where the cut was made.

The length of the slender dental bur head 60 enables the gauging of the depth during the cutting operation. For example, if the anomaly is located proximate a fissure 200 on the top surface 235 of an adult molar tooth the thickness may be known to be approximately 2.0 millimeters. The preferred length of the elongate dental bur head is 2.5 millimeters, and thus, the user is enabled to determine how far down the bur head 60 has cut into the enamel by observing the portion of the head which visibly extends above the enamel surface by subtracting the visibly extended portion of the head from 2.5 millimeters. Additionally, the user can determine how much uncut enamel remains until the dentinoenamel junction 255 is reached. The slender and elongate shape of the bur head 60 offers exceptional visibility to gauge the depth in the enamel while also making cuts sufficient to permit an explorer tool examine potential decay. Gauging the depth of the cut while using the bur and determining the thickness of the enamel advantageously aids in the prevention of unintentional over-cutting of the enamel beyond the dentinoenamel junction 255.

Figures 13, 14, 15, 16:
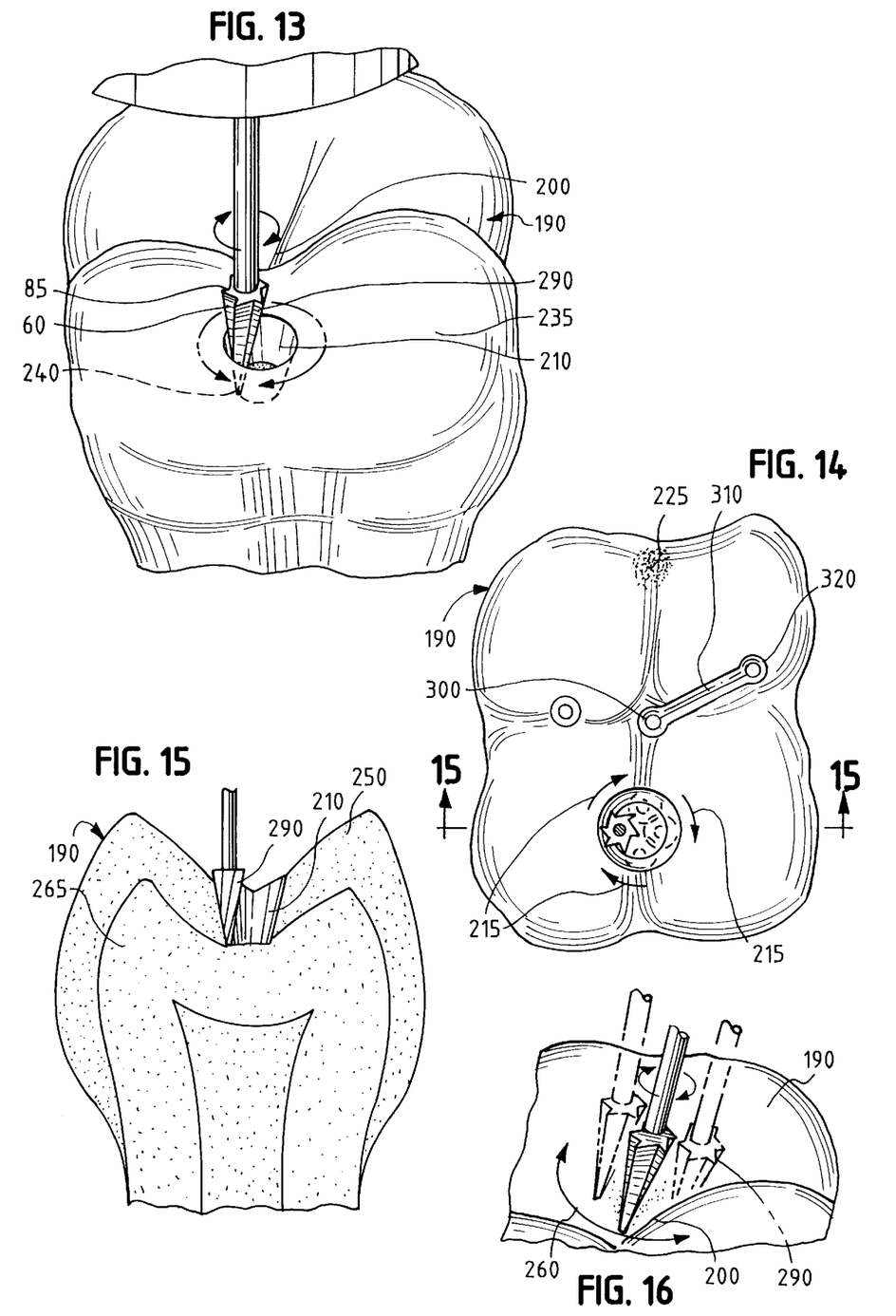
FIG. 13 is a perspective view of a tooth illustrating circular rotational movement of the dental bur to form an enlarged cut in the tooth.
FIG. 14 is a plan elevational view further illustrating the circular rotational movement of the bur to increase the size of the dental cut and illustrating a linear movement along a fissure of the tooth.
FIG. 15 is a cross sectional view taken along line 15—15 of FIG. 14.
FIG. 16 is a perspective view illustrating the sweeping motion of the dental bur along a fissure of a tooth to create a sweep cut.

Upon determining that the anomaly is a decalcification at a fissure 200 of the tooth 190, a sweep cut 260, as seen in FIG. 16, about the decalcified fissure may selectively be performed. In performing the sweep cut, the cutting blades 120 of the bur head 60 are laterally moved about the decalcified fissure portion 200 of the tooth 190 as seen in FIG. 16. The bur is laterally moved about the fissure in a semi-circular or arching manner such that the cutting blades 130 extending along the body 70 of the bur head 60 remove decalcified areas at the fissure 200 of the tooth 190. Preferably, the dental bur head 60 is laterally swept about the decalcified fissure 200 to a point at which the fissure coalesces. If coalescence is observed, then the examination often ends because no further decay or carious lesions are generally present. Otherwise, the sweep cut in the tooth continues so that the tooth can then be examined for the presence of further decay, Referring to FIGS. 10 and 11, the operation of performing and creating a plunge cut is shown. A plunge cut 270, FIG. 12, is preferably made upon determining that the anomaly is either a pit or a discoloration on the enamel surface 235 of the tooth 190. The plunge cut 270 is created upon the dental bur head 60 being moved in a downward direction such that the vertex moves toward the dentinoenamel junction 255 of the tooth 190. The vertex 80 of the bur head 60 is pointed in a downward direction, FIG. 11, and the head 60 is generally pushed straight down into the tooth 190 in line with the downward pointed direction for the vertex. The plunge cut may selectively be made to extend to the dentinoenamel junction 255 of the tooth. The dental bur 50 is then removed from the tooth 190 to examine the cut for the presence of carious lesions or further tooth decay. The slender conical dental bur head 60 provides dental cuts (plunge or sweep) having smooth slightly divergent wall surfaces which are easy to examine for tooth decay. The elongate conical dental bur 50 additionally significantly reduces or eliminates undesirable sidewall undercutting of an examined tooth. If it is determined that the no decay exists or if the decay has been removed from the tooth, then a flowable resin may selectively be used to fill the plunge cuts or sweep cuts made into the tooth 190.

Figures 10, 11, 12:
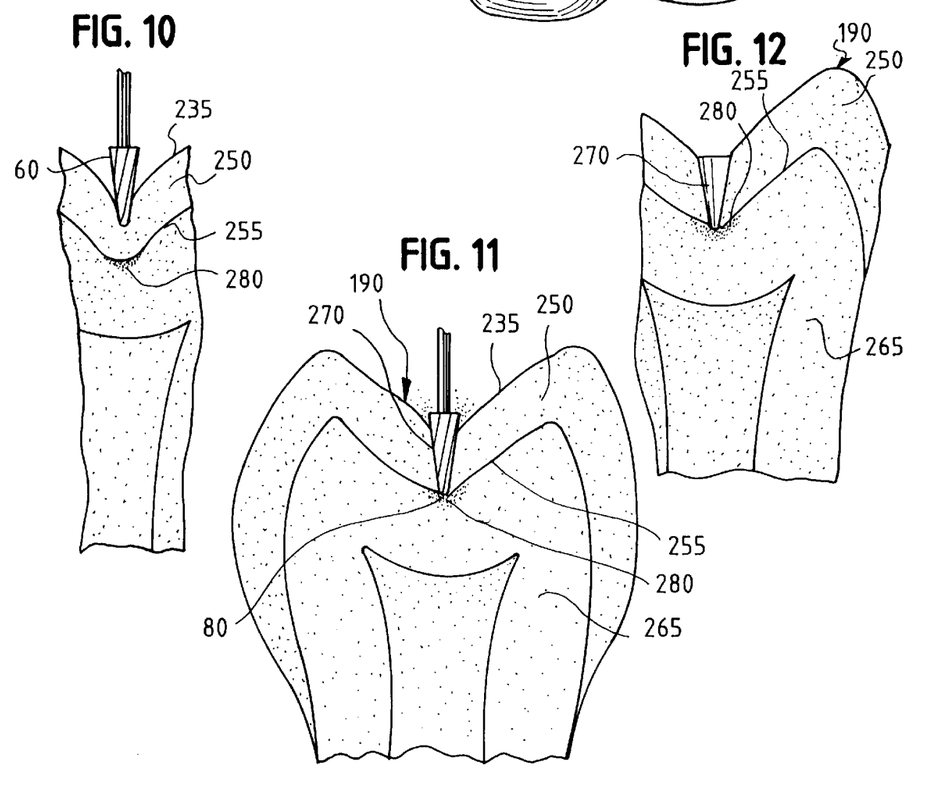
FIG. 10 is a partial cross sectional view of a tooth with the bur head inserted into the enamel of the tooth.
FIG. 11 is a cross sectional view of a tooth with the dental bur cutting to the dentinoenamel junction of the tooth.
FIG. 12 is a cross sectional view of the tooth of FIG. 11 with the dental bur removed.

Once the bur is employed to cut at anomalies in the diagnostic process, the cuts of the tooth (such as cut 270, FIG. 12) are further examined for the presence of carious lesions or "hidden caries 280, FIGS. 10–12." In order to further identify the existence of carious lesions 280 dentin caries dye may be applied to the tooth 190. A particular color (such as red) on certain areas of the tooth after a rinse will indicate the presence of carious lesions 280. A larger cut in the tooth may be required to remove any identified carious lesions or tooth decay. As seen in FIGS. 13–15, an extensive cut 210 into the tooth may be made by applying and engaging a wide portion 290 near the base 85 of the bur head 60 to the area of the tooth having the identified carious lesions. The size of an existing sweep cut or plunge cut may significantly be increased by applying the wide portion 290 near the top of the conical bur head 60.

As illustrated in FIGS. 13–15, the size of the dental cut may be increased by rotating the bur head 60, already inserted into the tooth 190, in a circular motion (as indicated by arrows 215, FIG. 14) to enable the wide portion 290 (FIG. 15) of the head 60 to remove areas of the tooth proximate the carious lesions. The tooth 190 having a large cut 210 may selectively be restored by filling the cut in the tooth with flowable resin. If required further preparation with another bur, such as a round diamond bur, is made and the restoration may selectively be completed with an amalgam material which requires a cut depth of at least 1.5 millimeters. As can be seen the slender conical shaped dental bur head 60 is able to effectively form numerous types and sizes of cuts in the examination of anomalies in the diagnostic process while also being effective in the removal of extensive carious lesions to further the restoration process of the tooth 190. As seen in FIG. 14, alternatively a plunge cut may selectively be made at pit 300 with the dental bur head 60 being moved laterally and linearly along a path 310 to connect to another pit 320. The path 310 is then examined for the presence of decay, for example, with an explorer tool and/or with a dentin carries dye.

While a detailed description of the preferred embodiment of the invention has been given, it should be appreciated that many variations can be made thereto without departing from the scope of the invention as set forth in the appended claims. For example, the cutting members can be comprised of diamonds or other durable cutting materials.

What is claimed is:

1. A bur for use in examining an anomaly in a tooth, comprising:

a bur head with a body having a base, an opposed vertex and outer surface; and a plurality of the cutting members located at the outer surface of the body with at least a portion of the cutting members being positioned between the base and vertex and extending along the outer surface with the bur head being at least 1.5 millimeters in length and in which at least one of the cutting members is a blade which extends over the vertex of the body beyond other cutting members at the outer surface of the body.

2. The bur of claim 1 in which the distance between the base and the vertex of the body ranges from 1.5 to 3 millimeters.

3. The bur of claim 1 in which the distance between the base and vertex is 2.5 millimeters.

4. The bur of claim 1 in which the body is formed of a carbide material.

5. The bur of claim 4 in which the cutting members are formed of a carbide material.

6. The bur of claim 5 wherein the bur head is generally conical in shape having a maximum diameter proximate the base and in which the diameter of the bur head gradually decreases as the body extends toward the vertex.

7. The bur of claim 6 in which the diameter of the conically shaped bur head ranges from 0.8 millimeters to 1.2 millimeters.

8. The bur of claim 7 wherein the cutting members are elongate blades which extend along the length of the body and in which the blades have a height extending outwardly from the body.

9. The bur of claim 8 in which the height of the blades varies as the blades extend along the length of the body.

10. The bur of claim 8 in which the height of the blades is substantially uniform as the blades extend from the base to the vertex of the body.

11. The bur of claim 1 in which the body has a longitudinal axis extending the length of the body of the bur and in which the bur head has a maximum diameter measured perpendicular to the longitudinal axis, and wherein
the ratio of the maximum diameter of the body to the length along the longitudinal axis of the body is no greater than 2.8:1.

12. The bur of claim 11 wherein the cutting members are a plurality of blades generally parallel to the longitudinal axis.

13. The bur of claim 12 including six blades positioned about the body of the bur head and in which two opposing blades of the six blades extend over the vertex of the body.

14. The bur of claim 12 wherein the blades have a generally helical shape with an angle in a range of 0° to 10°.

15. The bur of claim 12 wherein the blades have a rake angle of minus eight degrees.

16. The bur of claim 12 wherein the height of the blades vary as the blades extend longitudinally over the outer surface of the body.

17. The bur of claim 1 wherein the cutting members are arranged about the outer surface of the bur head to cut at a preselected variable cutting intensity along a longitudinal axis of the body.

18. The bur of claim 1 in which the body has a longitudinal axis and a drive shaft coaxially aligned with the longitudinal axis of the body and extending outwardly from the base for operating the bur at a preselected rotational speed, and
a cutting surface established at the cutting members connected to the body of the bur such that a cutting intensity is variable along the longitudinal axis of the body upon operating the bur at the preselected rotational speed.

19. The bur of claim 18 including a handpiece engaging the bur for rotating the bur at the preselected rotational speed, and
a dental unit operatively connected to the handpiece for providing operating power to the handpiece.

20. The bur of claim 1 wherein the plurality of cutting members are positioned along the body of the bur head having a conical shape which tapers from the base having a diameter ranging from 0.8 to 1.2 millimeters to a location proximate the opposed vertex having a diameter of approximately 0.013 inches such that the bur head is formed to cut and remove at least a portion of the anomaly.

21. The bur of claim 20 wherein the anomaly is at least one of:
(a) a fissure; (b) a pit; and (c) a discoloration, in an enamel portion of the tooth.

22. The bur of claim 20 wherein the cutting members are positioned to cut and remove the anomaly to a preselected distance in the tooth.

23. The bur of claim 22 wherein the preselected distance extends to at least a junction of the enamel portion and a dentin portion of the tooth.

24. A dental system for use in applying dental procedures to teeth comprising:
a dental unit connected to a hand piece for providing operating power to the hand piece;
an elongate dental bur having a bur head with a body, a vertex and a base, said bur is generally conical in shape having a maximum diameter proximate the base and in which the diameter of the bur head gradually decreases as the body extends towards the vertex, said base engages the hand piece such that the hand piece rotates the engages dental bur at a preselected rotational speed upon receipt of operating power from the dental unit; and
a plurality of cutting members positioned about an outer surface of the body of the bur head which extends for length ranging from 1.5 to 3 millimeters measured along a longitudinal axis of the body between the base and the vertex of the bur head.

25. The dental system of claim 24 in which the distance between the base and vertex along the longitudinal axis of the bur head is 2.5 millimeters.

26. The dental system of claim 24 in which both the body and the cutting members are formed of a carbide material.

27. The dental system of claim 24 including a hose connecting the dental unit and the handpiece for providing compressed air power to the handpiece.

28. The dental system of claim 27 in which the handpiece provides variable high speed rotation of the dental bur at speeds ranging from 300,000 to 350,000 rotations per minute.

29. A method of treating anomalies in teeth comprising the steps of;
utilizing a dental bur securable to a drive shaft of a high speed headpiece for performing diagnostic procedures to a tooth in which the bur has a bur head with a body which has a length ranging from 1.5 millimeters to 3 millimeters, said body of the bur head being generally conical in share having a narrow portion proximate a vertex of the bur head and a wide portion proximate a base of the bur head and a plurality of cutting members located about an outer surface of the body; and
performing restoration procedures to the tooth with the same dental bur.

30. The method of claim 29 in which the step of utilizing includes the step of identifying an anomaly at the tooth, and
exploring the anomaly with the dental bur.

31. The method of claim 30 including the step of applying the narrow portion of the bur head to the anomaly.

32. The method of claim 31 in which the cutting members of the bur head are formed of a carbide material.

33. The method of claim 32 including the step of determining if the anomaly is at least one of: (a) a decalcified fissure, (b) a pit and (c) a discoloration, in an enamel portion of the tooth.

34. The method of claim 33 including the step of directing the bur with the handpiece operatively powered to engage the anomaly to create a cut in the tooth at the anomaly.

35. The method of claim 34 including the step of gauging a depth of the cut in the enamel portion of the tooth based on the length of the bur head above an outer surface of the enamel and the location of the anomaly at the tooth.

36. The method of claim 35 including the step of performing a sweep cut about the decalcified fissure in response to determining that the anomaly is a decalcified fissure.

37. The method of claim 36 in which the step of performing the sweep cut includes the step of laterally moving the bur head about the decalcified fissure portion of the tooth to a point at which the fissure coalesces.

38. The method of claim 36 including the step of applying a flowable resin to fill the cut made in the tooth.

39. The method of claim 35 including the step of creating a plunge cut at the anomaly in which the bur cuts downward into the tooth upon the anomaly being either a pit or a discoloration at the enamel portion of the tooth.

40. The method of claim 39 in which the step of creating includes the step of pointing the vertex of the bur head in a downward direction, and pushing the bur head down into the tooth in line with the downward direction at which the vertex is pointed.

41. The method of claim 39 including the step of applying a flowable resin to fill the cut made into the tooth.

42. The method of claim 35 including the step of examining the cut for the presence of carious lesions.

43. The method of claim 42 including the step of applying carries dye to the tooth to identify the existence of carious lesions.

44. The method of claim 42 including the step of increasing the size of the cut by applying a wide portion of a base of the bur head to the area of the tooth having carious lesions.

45. The method of claim 44 in which the step of increasing the size of the cut includes the step of rotating the bur in a circular motion to enable the wide portion of the bur head to remove carious lesions of the tooth.

46. The method of claim 45 including the step of filling the cut in the tooth with an amalgam material.

* * * * *

UNITED STATES PATENT AND TRADEMARK OFFICE
CERTIFICATE OF CORRECTION

PATENT NO. : 6,257,889 B1  
APPLICATION NO. : 09/277216  
DATED : July 10, 2001  
INVENTOR(S) : Daniel W. Boston Page 1 of 3

It is certified that error appears in the above-identified patent and that said Letters Patent is hereby corrected as shown below:

Column 2, line 15, "without" should be changed to --with at--.

Column 2, line 51, "FIG. 8 is a plan elevational view of a tooth;" should be changed to --FIG. 8 is a perspective view illustrating the dental bur makIng an exploration cut to a tooth;--

Column 2, line 52-53, "FIG. 9 is a perspective view illustrating the dental bur making an exploration cut to a tooth;" should be changed to --FIG. 9 is a plan elevation view of a tooth;--

Column 3, line 14 "from the dental unit 20 Preferably," should be changed to --from the dental unit 20. Preferably,--

Column 3, lines 29-31, "is 0.013 inches at a location measured 0.005 inches" should be changed to --is 0.013 mm at a location measured 0.005 mm--.

Column 3, line 49, "inches" should be change to --millimeters--.

Column 3, line 51, "the longitudinal axis" should be changed to --the longitudinal axis 100--.

Column 3, line 52, "2.8:1" should be changed to --1:2.8--.

Column 3, line 53, "body 70, FIGS. 3-5" should be changed to --body 70, as shown in FIGS. 3-5,--.

Column 3, line 55, "body 70 of the and" should be changed to --body 70 and--.

Column 4, line 5, "located the outer surface" should be changed to --located at the outer surface--.

Column 4, line 21, "tip 180 in the cross section." should be changed to --tip in the cross section.--

Column 4, line 30, "proximate the drill tooth at the vertex" should be changed to --proximate the drill tooth 140 at the vertex--.

Column 5, line 35, "explorer tool examine" should be changed to --explorer tool to examine--.

UNITED STATES PATENT AND TRADEMARK OFFICE
CERTIFICATE OF CORRECTION

PATENT NO.         : 6,257,889 B1
APPLICATION NO.    : 09/277216
DATED              : July 10, 2001
INVENTOR(S)        : Daniel W. Boston It is certified that error appears in the above-identified patent and that said Letters Patent is hereby corrected as shown below:

Column 5, lines 47-48, "cutting blades 130" should be changed to --cutting blades 120--.

Column 6, line 64, "of the cutting members" should be changed to --of cutting members--.

In the drawings, sheet 2, FIG. 3, the dimension ".005 inches" should be changed to --.005 mm--.

In the drawings, sheet 2, FIG. 3, the dimension ".013 inches" should be changed to --.013 mm--.

Claim 1, column 6, line 64, "of the cutting members" should be changed to --of cutting members--.

Claim 2, column 7, line 5, "which the distance" should be changed to --which a distance--.

Claim 11, column 7, line 30, "extending the length" should be changed to --extending along the length--.

Claim 11, column 7, line 33, "the ratio" should be changed to --a ratio--.

Claim 11, column 7, line 35, "2.8:1." should be changed to --1 :2.8.--

Claim 16, column 7, lines 46-47, "height of the blades vary" should be changed to --height of the blades varies--.

Claim 24, column 8, line 28, "the engages dental bur" should be changed to --the engaged dental bur--

Claim 24, column 8, line 32, "which extends for" should be changed to --which extends for a--.

Claim 25, column 8, line 36, "the distance" should be changed to --a distance--.

Claim 29, column 8, line 51, "headpiece" should be changed to --handpiece--.

UNITED STATES PATENT AND TRADEMARK OFFICE
CERTIFICATE OF CORRECTION

PATENT NO. : 6,257,889 B1
APPLICATION NO. : 09/277216
DATED : July 10, 2001
INVENTOR(S) : Daniel W. Boston

It is certified that error appears in the above-identified patent and that said Letters Patent is hereby corrected as shown below:

Claim 29, column 8, line 55, "conical in share" should be changed to --conical in shape--.

Claim 35, column 9, line 11, "the location" should be changed to --a location--.

Signed and Sealed this

Fifth Day of February, 2008

JON W. DUDAS
*Director of the United States Patent and Trademark Office*